United States Patent [19]

Drews et al.

[11] Patent Number: 4,508,532
[45] Date of Patent: Apr. 2, 1985

[54] OPHTHALMIC ASPIRATOR/IRRIGATOR AND CYSTOTOME

[75] Inventors: Robert C. Drews; Danny D. Meyer; Tadmor Shalon; Eliezer Pasternak, all of St. Louis, Mo.

[73] Assignee: Ninetronix, Inc., St. Louis, Mo.

[21] Appl. No.: 530,730

[22] Filed: Sep. 9, 1983

[51] Int. Cl.³ .............................................. A61B 17/32
[52] U.S. Cl. .................................... 604/22; 604/155; 128/22
[58] Field of Search ............... 128/305; 604/22, 27, 604/30, 31, 35, 50, 51, 65, 67, 155, 222, 246

[56] References Cited

U.S. PATENT DOCUMENTS

| | | | |
|---|---|---|---|
| 3,930,505 | 1/1976 | Wallach | 604/22 |
| 3,996,935 | 12/1976 | Banko | 604/22 |
| 4,167,943 | 9/1979 | Banko | 604/22 X |
| 4,320,761 | 3/1982 | Haddad | 604/22 X |
| 4,338,932 | 7/1982 | Georgi et al. | 604/31 X |
| 4,345,595 | 8/1982 | Whitney et al. | 604/31 |
| 4,402,310 | 9/1983 | Kimura | 604/35 X |
| 4,409,966 | 10/1983 | Lambrecht et al. | 604/50 X |
| 4,428,748 | 1/1984 | Reyman et al. | 604/22 |

Primary Examiner—Edward M. Coven
Attorney, Agent, or Firm—Harness, Dickey & Pierce

[57] ABSTRACT

An ophthalmic aspirator and cystotome having a handheld, motorized instrument which is operated by a battery-run control system. The instrument includes a disposable coaxial aspirator-irrigator tip and a wormdrive mechanism for bidirectional, variable speed operation and also includes a disposable scalpel tip with infusion-/irrigation orifice for communication with an intraveneous solution bag. The scalpel tip is coupled through a clutch mechanism to the motor, which may be adjusted by the control system to make single or repeated cuts in either of two rotary directions. The aspirator's most frequently needed controls are mounted on the handpiece to provide an easily operable instrument of great precision for use in eye surgery. The instrument features an electronic control circuit housed in part within a desk top or suspendable unit and in part within the handpiece. The circuit may be switched between the aspirator mode and the cystotome mode and provides control signals to a motor carried within the handpiece. In the aspirator mode the circuit generates aspirate and backflush signals at the touch of a control switch mounted on the handpiece. Flow rates are continuously variable by means of a potentiometer control in the butt of the handpiece. In the cystotome mode the control switch commands either single cutting strokes or repeated cutting strokes in either of two rotary directions, the direction being selected by the potentiometer control.

16 Claims, 17 Drawing Figures

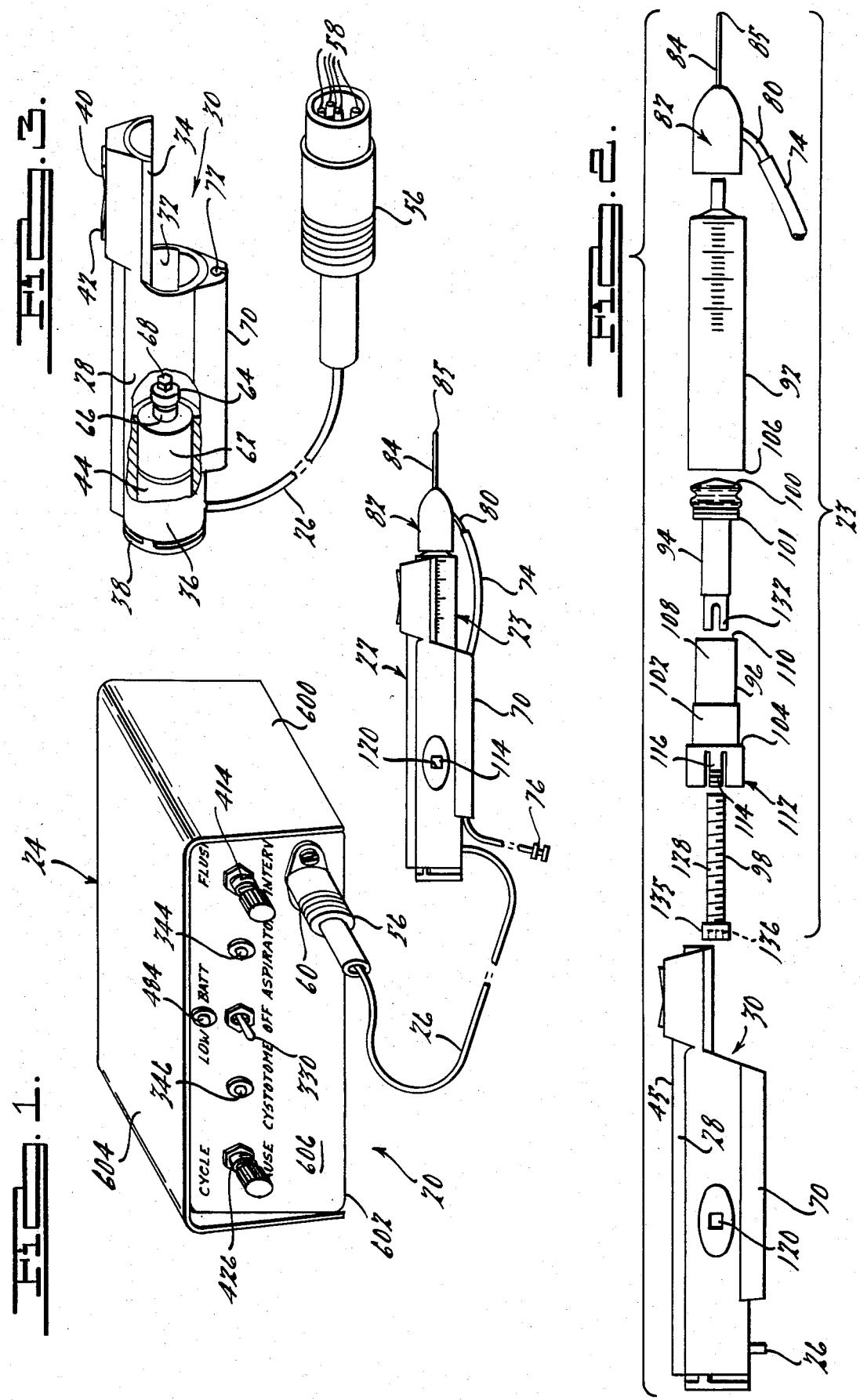

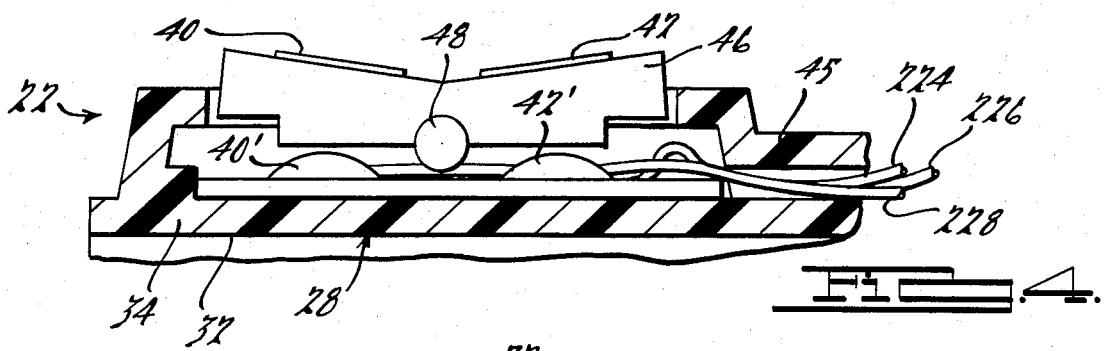
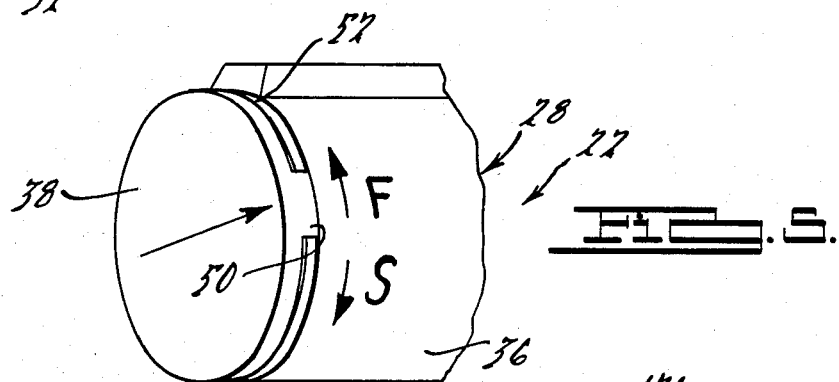
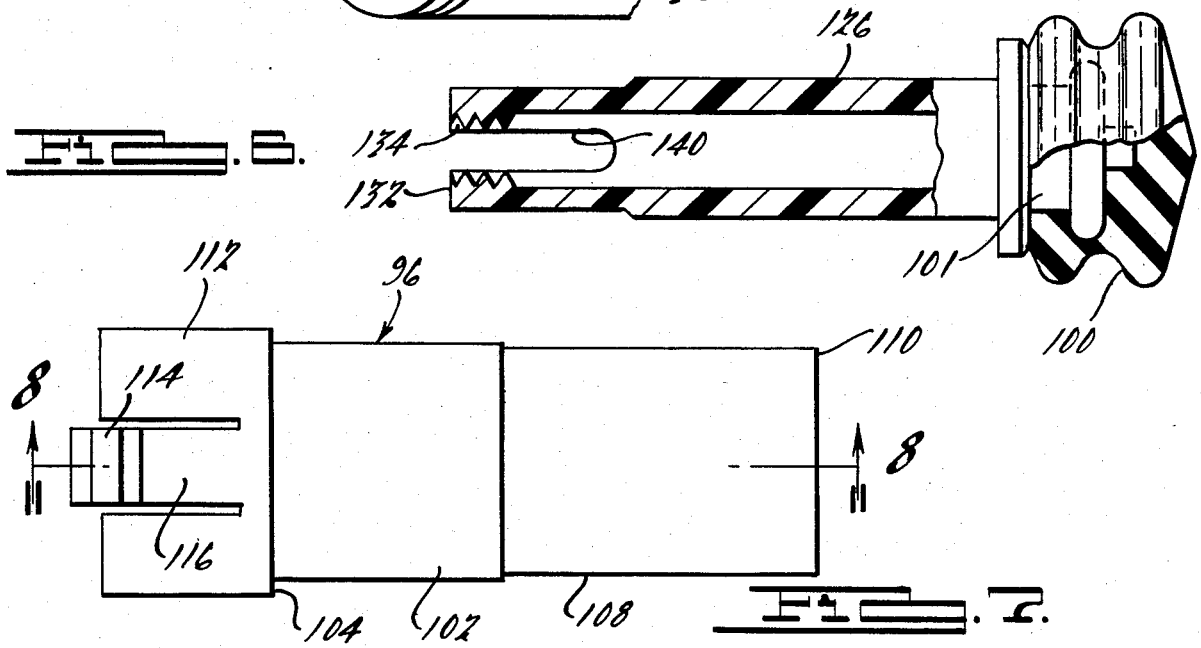
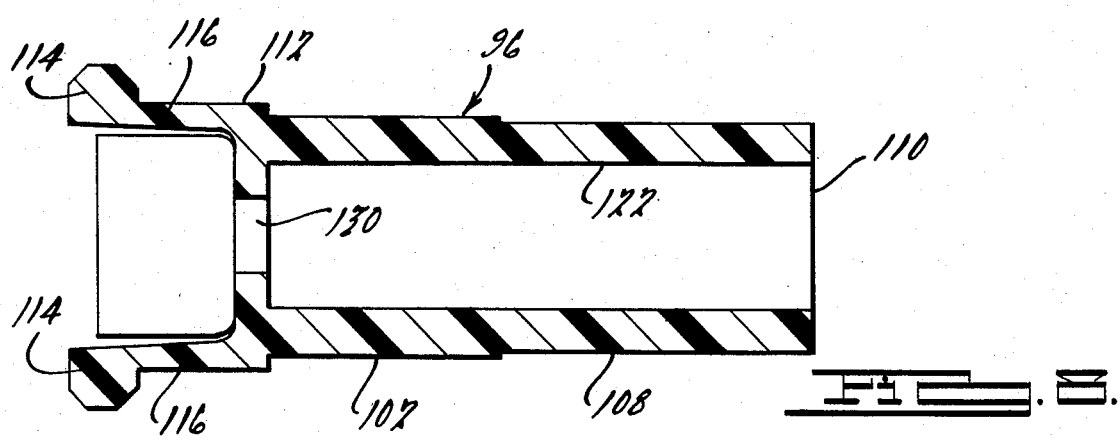

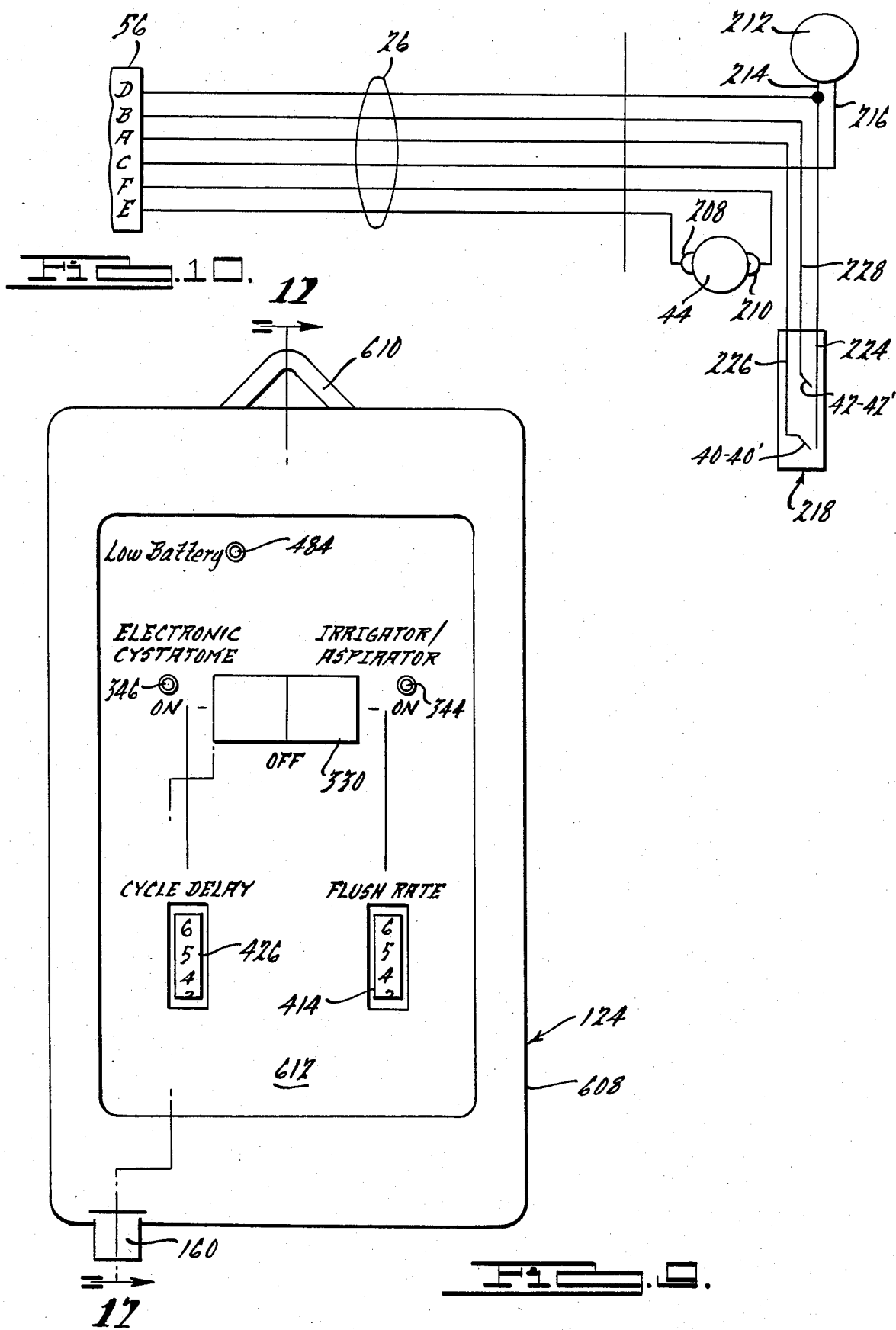

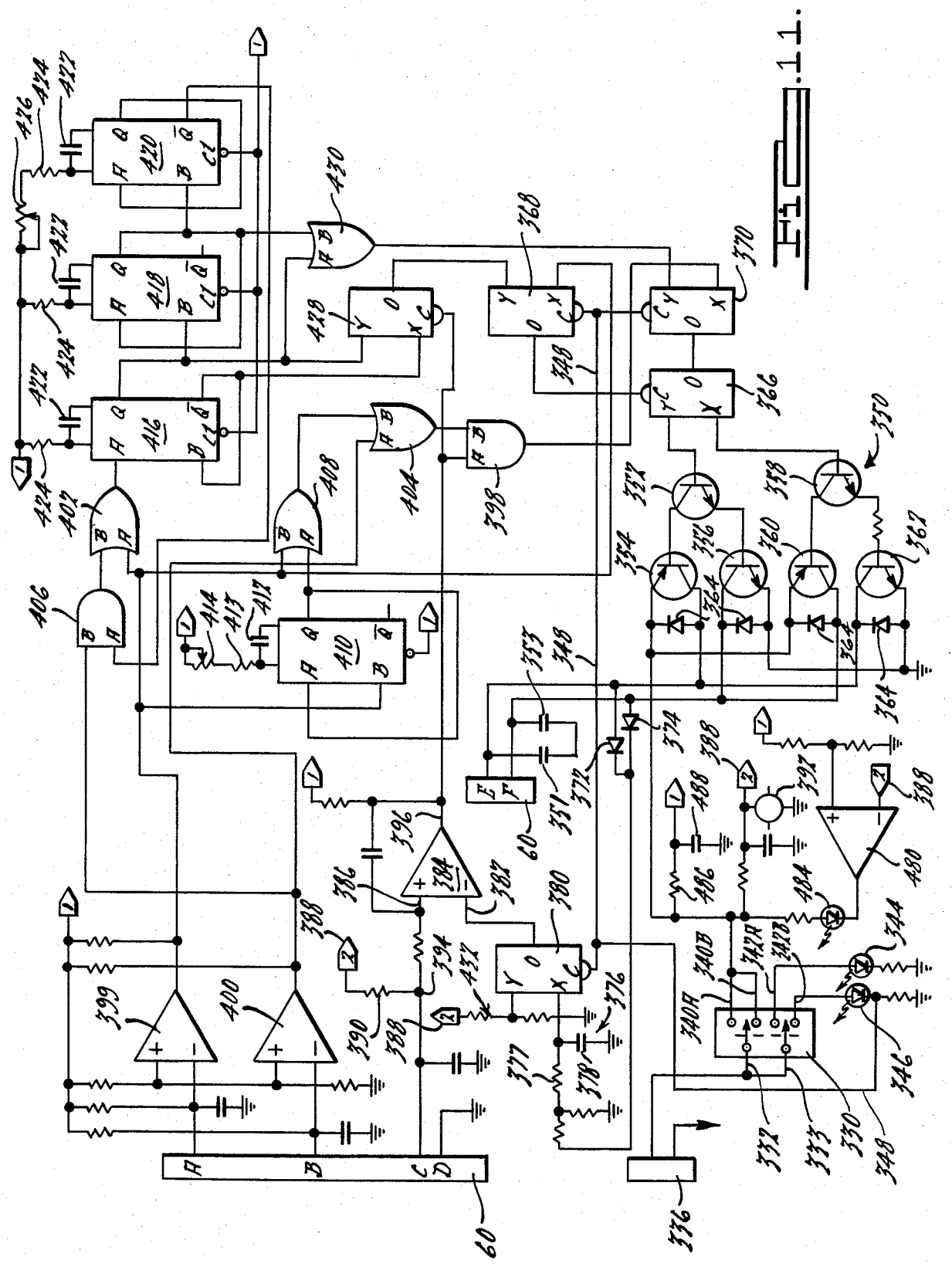

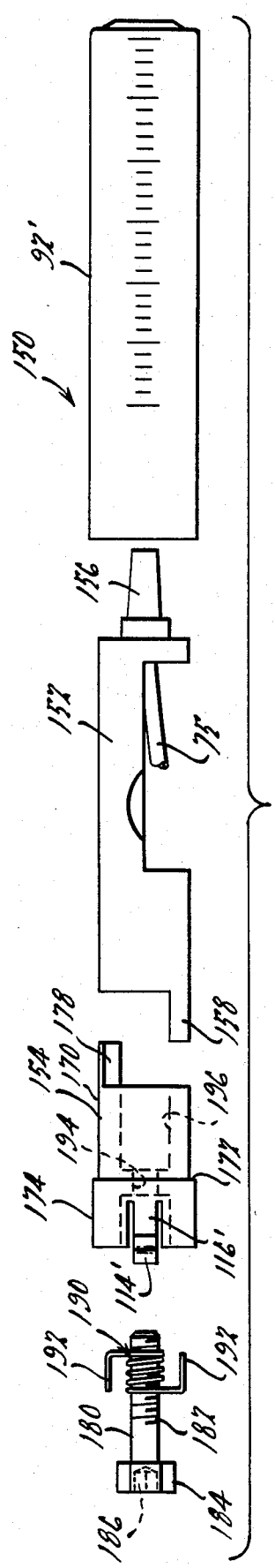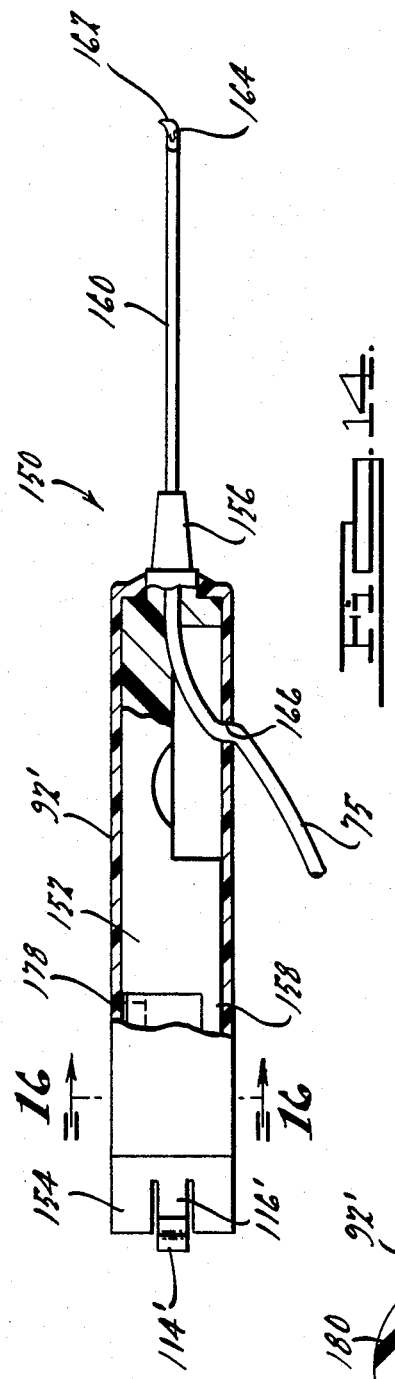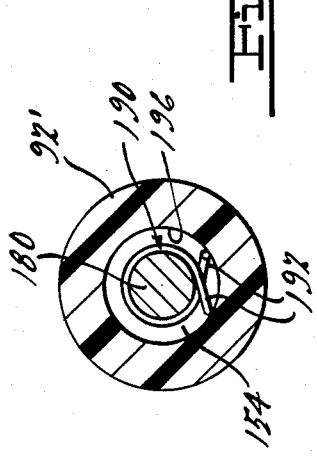

OPHTHALMIC ASPIRATOR/IRRIGATOR AND CYSTOTOME

BACKGROUND—SUMMARY OF THE INVENTION

The present invention relates to a medical instrument particularly adapted for use in ophthalmic surgery. During extracapsular cataract surgery, it is necessary for the surgeon to perform many operations with small and delicate instruments viewed through a microscope. At the present time, the break-up and removal of the cataractous and other tissue from the eye, as well as the continuous substitution of fluids back into the eye to maintain appropriate internal pressure, is typically carried out with manually operated hand-held instruments. The delicateness and precision with which ophthalmic surgery is performed requires highly durable precision instruments which are capable of performing the same precise function in the same way every time.

Modern extracapsular cataract surgery involves the removal of the cortex of the cataract by an "aspirator" instrument while at the same time utilizes an infusion system for keeping the anterior segment of the eye filled with fluid and safe from collapse. The aspiration instrument removes the cortex and also engages and frees strands of cortex to either aspirate them or flush them from the eye using irrigation. A cystotome instrument is also utilized during cataract surgery to cut open the lens and assist in the removal of the cataractous tissue.

A variety of aspirating, infusion and cystotome systems and instruments are in use today for assisting in ophthalmic surgery, particularly extracapsular cataract surgery. Separate aspirating cannulas, separate sources of aspiration pressure, and separate infusion cannulas are often utilized in the same operation, although some surgeons use instruments which combine the aspiration and irrigation functions. Manually operated syringes to generate aspiration and control functions are also utilized. Not only do these systems often utilize separate devices to perform the various functions, but the devices usually require the use of both hands of the surgeon, leaving him without a free hand to perform other tasks or steady the instrument. Also, the required manual operation of these instruments is often tiring to the surgeon and can lead to some imprecision.

Pump mechanisms are often utilized to provide the aspiration, but these are usually controlled by foot pedals which are often complex to operate and sometimes difficult to find easily under operating room conditions. The foot switch activated pumps are also connected to the aspiration cannula by long flexible tubing which can cause fluctuations in the aspiration pressures and brief time delays in the operation of the instruments.

Present cystotome instruments for extracapsular cataract surgery are also typically manually operated. Again, these instruments can be fatiguing to the surgeon and could cause imprecision in the operation thereof.

The present invention has been developed and designed to overcome the problems associated with present systems and instruments for ophthalmic surgery, particularly extracapsular cataract surgery. It provides an automatically operated device which can be held and operated in one hand by the surgeon, provides the same precision function continuously and repeatably (of either aspiration, irrigation, or cystotome procedures), and utilizes disposable parts to maximize sterility and cleanliness.

It is an object of the present invention to provide an efficient, precise, easily operable instrument for use during eye surgery and removal of cataracts. It is another object to provide an instrument which can be held and operated in one hand by the surgeon and which does not utilize foot pedal controls or long tubing in operation. It is still another object of the invention to provide an instrument for extracapsular cataract surgery which utilizes disposable parts wherever possible, is lightweight, is reliable in performance, has variable speed controls, and has a back flush feature (for example, to release accidentally engaged tissue). A further object of the present invention is to combine convenience, flexibility and precise control for a procedure which demands optimization of all of the above-mentioned features for precision and safety.

In accordance with the present invention, a hand-held motorized instrument is provided which is operated by a battery-run control system. The body portion has a worm-drive mechanism for speed and direction controls, and is adapted to operate either an aspirator or cystotome instrument insert which is affixed in place in the instrument. As an aspirator, a syringe type mechanism is utilized with a coaxial aspirator-irrigator tip. The plunger of the mechanism moves in either direction, at a variable controlled rate of speed, and has a back flush option which automatically reverses the aspiration cycle when the control button is released. As a cystotome, the insert mechanism has a rotatable cannula tip which can be rotated in either direction, either continuously or one cutting stroke at a time.

Other objects, features and advantages of the present invention will be apparent from the following disclosure taken in conjunction with the accompanying drawings and appended claims.

BRIEF DESCRIPTION OF THE DRAWINGS

FIG. 1 is a schematic overall view of the invention with an aspirator-irrigation instrument insert;

FIG. 2 is an exploded view of the inventive hand-held instrument and aspirator-irrigation instrument insert;

FIG. 3 is a perspective view of the handpiece with the motor mechanism shown in partially broken-away section;

FIG. 4 depicts the top-mounted pushbutton mechanism for the handpiece;

FIG. 5 depicts the speed-direction control at the butt end of the handpiece;

FIG. 6 is a side view partially in cross-section of the piston mechanism of the aspirator-irrigation instrument insert;

FIG. 7 is a side view of the trunnion mechanism of the aspirator-irrigation instrument insert;

FIG. 8 is a cross-sectional view of the trunnion mechanism of FIG. 7, taken along the line 8—8 and in the direction of the arrows;

FIG. 9 is a plan view of the control device for the hand-held instrument;

FIG. 10 is a circuit diagram for the electrical circuit in the handpiece;

FIG. 11 is a circuit digram for the control device;

FIG. 14 illustrates the cystotome insert for the handpiece in partially broken-away section;

FIG. 15 is an exploded view of the cystotome insert mechanism for use with the handpiece;

FIG. 16 is a cross-sectional view of the cystotome insert of FIG. 14, taken along the line 16—16 and in the direction of the arrows.

DESCRIPTION OF THE PREFERRED EMBODIMENTS

Figure 17:
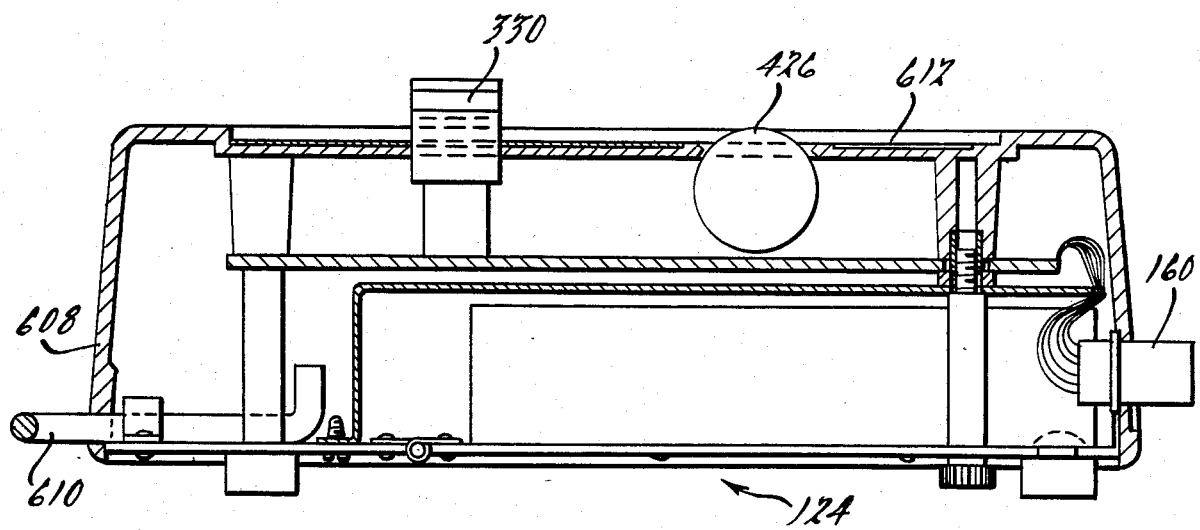
FIG. 17 is a cross-sectional view of the control device of FIG. 9, taken along the line 17—17.

The extracapsular cataract removal instrument and system is referred to generally by the numeral 20 in the drawings (see FIG. 1). The system generally comprises a hand-held instrument 22 and a control device 24 connected together by wire cable or conduit 26. FIG. 1 shows one embodiment of the control device 24 with the various switches and controls on the face. An alternate (and preferred) embodiment of the control device is shown in FIGS. 9 and 17 and referenced by the numeral 124. Both control devices 24 and 124 have the same internal circuitry and perform the same functions, as described hereinafter, and only differ in size, shape, and type of external operating switches and controls.

More specifically, the control device 24 shown in FIG. 1 comprises cabinet 600 constructed, for example, of a U-shaped sheet metal lower member 602, defining the front, bottom and back panels, and an inverted U-shaped sheet metal upper member 604 forming the side panels and top of the cabinet. Cabinet 600 houses a plurality of electronic components which make up control device 24, discussed more fully below, and also houses the batteries which power the unit. Cabinet 600 includes a front panel 606 upon which are mounted the following components and controls: female socket or jack 60, low battery indicator light or LED 484, aspirator mode light or LED 344, cystotome mode indicator light or LED 346, flush interval controller knob or potentiometer 414, and cycle pause adjustment knob or potentiometer 426, and mode selector switch 330. A more complete description of these components and controls is set forth below.

The alternate and presently preferred control device 124, shown in FIG. 9, comprises a rectangular cabinet 608 which includes a retractable bale 610, or the like, for hanging the controller on a pole such as the type used to suspend intraveneous solution (I.V.) bottles. Cabinet 608 includes front panel 612 upon which the following components and controls are mounted: low battery indicator light or LED 484, cystotome mode indicator light or LED 346, aspirator mode indicator light or LED 344, mode selection switch 330, cycle delay controller or potentiometer 426 and flush rate controller or potentiometer 414. To provide a neat appearance and low profile, mode selector switch 330 may be implemented using an on-off-on rocker switch and cycle delay controller 426 and flush rate controller 414 may be implemented using thumb wheel potentiometers. A female socket or jack 160 is provided on the bottom of the cabinet. The case or cabinet 608 houses a plurality of components which make up control device 124 as well as the batteries for powering the unit.

The handpiece 22 is of a size and weight to fit easily within a person's hand. It can be made of any durable material, such as metal, plastic or the like, but preferably is molded from a thermoplastic material into a shape similar to that shown in FIGS. 2 and 3. The handpiece 22 has a hollow body portion 28 which has a front opening 30 and central chamber 32 into which the aspirator-irrigator instrument insert 23 or cystotome instrument insert 150 (as described below) can be positioned. The lower part of the front end 34 of the body portion 28 is cut away for ease of insertion and removal of the instrument inserts. The positioning of one of the inserts in the handpiece (in this case the aspirator-irrigator insert 23) is shown in FIG. 1.

The rear or butt end 36 of the handpiece 22 has a speed/direction control knob 38 which is further shown in FIG. 5 and described in more detail hereinafter. A pair of control switches (pushbuttons) 40 and 42 are positioned on the upper surface at the front end 34 of the handpiece. As shown in FIG. 4, the control buttons 40 and 42 are positioned on a rocker or lever mechanism 46 which pivots or rotates around pivot 48. The ends of pivot pin 48 are positioned in sockets in the sides of the body portion 28. The bottom edges of the rocker mechanism 46 are adapted to operate pressure switches 40' and 42' positioned directly below the pushbuttons 40 and 42. The pressure switches are connected by wires or leads (224, 226 and 228) to the control circuitry yet to be discussed. The wires or leads are positioned inside ridge 45 on the upper surface of the handpiece and are coupled to or extend through conduit 26. When the operator pushes on button 40 or 42, the rocker mechanism 46 rotates around pivot pin 48 and activates the corresponding pressure switch 40' or 42'.

As will be described later, when the aspirator-irrigator instrument insert 23 is positioned in the handpiece 22 and the control device 24, 124 is set in the corresponding mode of operation, the front-most pushbutton 40 operates the aspirator function of the insert while the second pushbutton 42 operates the ejection function. On the other hand, when the cystotome instrument insert 150 is positioned in the handpiece and the control device is switched to the cystotome mode of operation, the pushbutton 40 operates a single cutting stroke of the cystotome scalpel while the pushbutton 42 operates continuous or repeated cutting strokes.

The control knob 38 is connected to a potentiometer 212 (rheostat) and rotates relative to the body portion 28 of the handpiece 22. The knob 38 has an ear or tab 50 which is adapted to meet and abut against stop 52 to prevent complete rotation of the control knob. The stop 52 also sets the maximum limits of the speed/direction control for the system. The knob 38 regulates the speed of the aspirator mechanism when the control device 24, 124 is set in that mode of operation and the aspirator instrument insert 23 is positioned in place in the body portion 28. The control knob 38 controls the cutting direction of the cystotome when the control device 24, 124 is set in the cystotome mode of operation and the cystotome instrument insert 150 is positioned in place in the body portion.

The handpiece 22 is connected to the control device 24 (or 124) by wire cable or conduit 26 and connector plug 56. The plug 56 is of conventional type and has a plurality of pins 58 corresponding to the number of wires and conductors carried in the wire conduit 26. The control device has a mating female socket (jack) 60 on one face or end and the plug 56 can be conveniently connected and disconnected from it. (In FIG. 9, the jack is designated by reference numeral 160.)

The motor 44 for controlling the operation of the handpiece instrument insert is securely positioned at the rear end of the chamber 32 in the body portion 28. This is shown in FIG. 3. The activation and operation of the motor 44 is controlled by the control device 24 (or 124), as explained below. Preferably the motor is a small 4 volt DC supply voltage (nominal) motor, Model Series 1212E—004G, made by MicroMo Electronics, Inc., St. Petersburg, Fla. A screw-on gearhead 62 is attached to the motor and regulates the operation of the insert. Preferably, the gearhead is Model Series 12/1 with a 330:1 gear ratio, also made by MicroMo Electronics, Inc. A hex-head member 64 is secured on the end of the shaft 66 from the motor 44 and gearhead 62. The hex-head member 64 has a hexagonal tip 68 which is adapted to mate with the ends of the screw-type drive members which are in effect the drive shafts for the handpiece instrument inserts.

A ridge 70 is positioned on the bottom of the body portion 28 of the handpiece 22. The ridge 70 helps the operator to grasp and hold the handpiece. Also, a central slot or passageway 72 can be provided in the ridge 70 for holding a tube, such as infusion/irrigation tube 74 used with the aspirator instrument insert, or such as infusion/irrigation tube 75 used with the cystotome instrument insert 150 (FIGS. 14-16). When the aspirator-irrigator instrument insert is used, the tube 74 is connected at one end by means of connector 76 to an intravenous solution bag (not shown) and connected at its other end to metal tube 80 protruding from cannula member 82. The tube 80 in turn is in fluid communication with the outer coaxial cannula tube 84 and, when the cannula is inserted into the eye, returns the necessary fluid to the eye to replace the fluid being aspirated and thus maintain proper pressure.

An exploded view of the aspirator-irrigator instrument insert 23 is shown in FIG. 2. More detailed views of portions of the aspirator insert are shown in FIGS. 6-8. The aspirator-irrigator instrument insert 23 includes a syringe-type tube 92, a drive shaft 98, and a cannular member 82. The piston 94 has a rubber tip 100 positioned on the head 101 which makes sealing contact with the inner walls of the syringe-type tube 92.

The trunnion 96 is adapted to fit tightly in the open end of the tube 92. For this purpose, the central portion 102 of the trunnion has a diameter essentially the same as the inner diameter of the tube 92. The shoulder 104 on the trunnion 96 seats firmly against the end 106 of the tube 92. The smallest diameter portion 108 of the trunnion fits easily within the tube and acts as a sleeve around the piston 94. The end 110 of the trunnion limits the rearward movement of the head 101 of the piston 94. The trunnion has a head 112 at the other end. The head 112 has a pair of outwardly extending ears or nubs 114 which are formed on the end of spring-like flange members 116. When the aspirator-irrigator instrument insert 23 is positioned in the body portion 28 of the handpiece 22, the two nubs 114 mate with a pair of opposed apertures 120 in the sides of the body portion 28 of the handpiece. This removably locks the instrument insert in the handpiece.

For removal of the instrument insert from the handpiece (i.e., for disposal, for insertion of another insert, etc.), the operator simply has to push inwardly on the two opposed nubs 114 freeing them from the apertures 120 and then grasp the insert under the front part 34 of the handpiece body portion 28 and pull it out of the chamber 32. As can be seen, a quick and easy method for inserting, removing, and changing various instrument inserts in the handpiece 22 is provided with the present invention.

The trunnion 96 is hollow with a central passageway 122 partially therethrough. The body 126 of the piston 94 is sized to easily fit and slide within the passageway 122 when the aspirator-irrigator instrument insert 23 is assembled. The drive shaft 98, which preferably is a machine screw or the equivalent thereof, connects the trunnion and piston together. The stem or shaft 128 of the drive shaft 98 fits through opening 130 at the end of passageway 122 in trunnion 96 and mates with the end 132 of the piston 94. For this purpose, the drive shaft 98 is threaded and mating threads 134 are provided on the inner surface of one end of the piston 94.

The drive shaft has a plastic machine screw type head 135 thereon with a hexagonal shaped socket 136 in it. The socket 136 is adapted to mate with the hex tip 68 on the end of the motor shaft 66 when the instrument insert 23 is positioned in the body portion of the handpiece. In this manner, when the motor is activated and the hex tip rotated, the drive shaft 98 is caused to rotate also. The drive shaft in turn threadedly moves the piston longitudinally along the longitudinal axis of the syringe-type tube 92. Due to the seal made by the rubber head 100 of the piston 94 in the tube 92, a vacuum or suction is created when the piston is moved away from the cannula member 82 at the front end of the instrument insert. This is turn pulls (aspirates) the material from the inside of the eye. The vacuum is established in the inner coaxial tube 85 of the cannula member.

The end 132 of the piston 94 is formed with a pair of opposed longitudinal slots 140. The slots 140 act as a safety mechanism so that when piston is driven to either extreme, the assembly will not be ejected from handpiece or destroyed. This also prevents the threads from stripping if an obstacle or obstruction is met which prevents the piston 94 from moving.

The cystotome instrument insert 150 is shown in partial cross-section in FIG. 14. The insert 150 includes a syringe-type tube 92' which is similar to the syringe-type tube 92 used in the aspirator-irrigator instrument insert 23. The insert 150 also includes a rotating member 152 and a stationary retaining member 154 for retaining the rotating member. The rotating member is sized to fit easily within the enclosing syringe-type tube 92' and has a cone-shaped hub member 156 on one end (front) and an outwardly extending flange 158 on the other end.

A cystotome instrument 160 with a scalpel-knife edge 162 is attached to the cone-shaped member 156 and protrudes outwardly therefrom. The cystotome instrument 160 is hollow and also acts as an infusion/irrigator device to maintain eye chamber pressure. When the instrument 160 is positioned in the eye, fluid can be inserted or injected into the eye through opening 164 at or adjacent the cutting end or scalpel edge 162. A tube 75 connects an intravenous solution bag (not shown) to the instrument 160. The tube 75 passes through an opening 166 in the wall of the syringe-type tube 92'.

The stationary retaining member 154 has a main body portion 170 which fits snugly inside the tube 92'. Shoulder 172 on the head 174 of the member 154 is adapted to abut against the end 176 of the tube 92' when the cystotome instrument insert 150 is assembled together (as shown in FIG. 14). The stationary retaining member 154 has a flange 178 which protrudes into the tube 92'.

The stationary retaining member 154 also has a pair of oppositely disposed ears or nubs 114' on spring-like flange members 116'. The nubs 114' and flange members 116' are substantially the same as the nubs 114 and flange members 116 described above with reference to the aspirator-irrigator instrument insert 23 and function in the same manner. The nubs 114' and flange members 116' are adapted to mate with and be releasably snap-locked into the aperture 120 in the body portion 28 of the handpiece 22. In this manner, the cystotome instrument 150 can be assembled into the handpiece 22 and be operated thereby.

A drive pin 180 is used to operate the cystotome instrument insert 150. The drive pin is a machine screw or the equivalent thereof with an elongated stem or shaft 182 and a head 184. A hexagonal shaped socket 186 is provided in the head 184 and is adapted to mate with the hex tip 68 on the end of the motor shaft 66 when the insert 150 is positioned in the body portion 28 of the handpiece 22. A clutch mechanism 190 is provided on the stem of the drive pin 180. The drive and clutch mechanism is best shown in FIGS. 15 and 16. The mechanism 190 consists of a coil of wire wrapped tightly around the drive pin stem and has two outwardly extending bent ends 192. When the drive pin is inserted through the opening 194 in the actuating member 154, the clutch mechanism 190 is tightly positioned on the stem 182.

When the cystotome instrument insert 150 is positioned in place in the handpiece 22, the cutting end 162 can be rotated partially to provide short cutting strokes. When the motor 44 is activated, the hex-tip 68 rotates the drive pin 180 which in turn through the spring loaded clutch mechanism 190 rotates the flange 158 on rotating member 152 and in turn rotate member 152. The rotation of member 152 in turn directly rotates the cutting end 162 of the cystotome instrument. After a time delay, which lets hub 156 rotate through approximately 90 degrees, the drive motor 44 reverses direction and returns to its rest position. At that point the tightly wound spring 190 is relieved when one of the ears 192 strikes member 178 and causes the spring to slightly unwind thus stopping the transmission of power from drive pin 180 to member 152.

As indicated earlier, the control device 24 (or 124) controls the operation of the cystotome instrument insert 150 through pushbuttons 40 and 42. When button 40 is activated, a single cutting stroke of the cutting end 162 takes place. At the end of the stroke, the cutting end returns to its "rest" postion. When button 42 is activated, the cutting end 162 operates a continuous series or repetition of cutting and return strokes until pressure on the button is released. The operator thus has the option of utilizing single or continuous strokes of the cystotome during surgery.

When the insert 150 is positioned in the handpiece and the control device is set for the cystotome mode of operation, the invention also allows the surgeon-operator to select the direction of the cutting stroke of the scalpel-knife. In the cystotome mode, the control knob 38 is adapted to direct and change the direction of the cutting stroke from clockwise to counter-clockwise and vice-versa. When the control knob 38 is turned clockwise to its stopping point (with tab 50 abutting against stop 52), the cystotome instrument 160 will rotate in clockwise cutting strokes. The instrument 160 rotates in a counter-clockwise direction when the control knob is turned in the other direction.

The preferred electronic control circuit of the present invention is housed in part within the control device 24 (or 124) and in part within the handpiece 22. FIG. 11 illustrates schematically that portion of the circuit which resides within the control device, while FIG. 10 illustrates that portion of the circuit which resides within the handpiece. These respective circuit portions are intercoupled through a six-conductor electrical cable or conduit 26 as shown in FIG. 10. To enable the handpiece 22 to be electrically disconnected from the control device for transportation, storage or replacement, cable 26 includes plug 56 which is removably coupled to jack 60 (or 160) mounted on the control device 24 (or 124). Both plug 56 and jack 60 include six terminals designated A through F in FIGS. 10 and 11. In particular, it will be noted that in FIG. 11 jack 60 has been schematically broken into two parts which appear at different locations in the drawing for illustration purposes only.

Directing attention first to the electrical components housed within the handpiece 22, FIG. 10 illustrates bidirectional motor 44 having a first electrical terminal 208 coupled to terminal E of jack 60 and having a second electrical terminal 210 coupled to terminal F of plug 60. In the preferred embodiment, motor 44 is a DC motor operable on a nominal supply voltage of four volts and capable of speeds up to 15,000 rpm at torques up to 0.014 oz.-in. As indicated above, motor 44 may be implemented using motor type 1212E/004G manufactured by MicroMo Electronics, Inc., St. Petersburgh, Fla.

The electronic circuit housed within the handpiece 22 further comprises potentiometer 212 having a first terminal 214 connected to terminal D of plug 60 and having a second terminal 216 connected to C of plug 60. Potentiometer 212 is directly connected to control knob 38 and is manually adjustable to control the driving speed of motor 44. The circuit further includes switch assembly 218 comprising front switch 40–40' and back switch 42–42'. Switch assembly 218 includes a common lead 224 coupled to terminal D of plug 60, a front switch lead 226 coupled to terminal A of plug 60, and a back switch lead 228 coupled to terminal B of plug 60. Front and back switches 40–40' and 42–42' are of the normally open type; pressing either switch couples the corresponding switch lead to common lead 24. For example, depressing switch 40–40' completes a circuit between terminals A and D of plug 60, while depressing switch 42–42' completes a circuit between terminals B and D of plug 60.

Referring now to FIG. 11, the remainder of the electrical control circuit will now be described in detail. In order to select between the aspirator mode and the cystotome mode switch 330 is provided. Switch 330 is preferably an on-off-on double pole double throw switch having first and second common terminals 332 and 333 mutually coupled to a source of DC electrical current. Preferably this source of DC electrical current is supplied through a jack such as jack 336 having a ground lead 338 and a hot lead 340. In practice jack 336 may be coupled to a battery power supply such as four series connected 1.5 volt, C-size dry cells (not shown). Switch 330 includes a first pair of alternately selectable terminals 340A and 340B, and a second pair of alternately selectable terminals 342A and 342B. Terminal 342A is connected to light emitting diode assembly 344 which, when lit, indicates that the aspirator mode has been selected and terminal 342B is connected to light emitting diode assembly 346 which, when lit, indicates that the cystotome mode has been selected. Terminals 340A and 340B are coupled together and supply electrical power to the control circuit when either the aspirator mode or the cystotome mode has been selected. Bus 348 is coupled to light emitting diode assembly 346 such that a low logic signal is placed on bus 348 when the unit is in the aspirator mode and a high logic signal is placed on the bus when the unit is in the cystotome mode. The logic signals placed on this bus are used to toggle certain components between states as will be more fully discussed below.

The motor drive circuit comprises transistor bridge 350 and capacitors 351 and 353. To drive the motor in a clockwise direction, a signal is applied to transistor 352 which in turn activates transistors 354 and 356. When transistors 354 and 356 are activated, a circuit path is completed from the battery source of electrical current to motor 44 with a right polarity. Current flows through the motor in a given direction causing the motor to turn clockwise. To drive the motor counter-clockwise, a signal is applied to transistor 358 which in turn activates transistors 360 and 362. Activating transistors 360 and 362 completes a current path from the battery supply to motor 44 with a reverse polarity. Current flows through motor 44 in a direction opposite to that described above and the motor turns counter-clockwise. Diodes 364 are provided to protect the motor drive transistors from inductive spikes which might otherwise damage the transistors.

The motor drive circuit is controlled by a logic circuit comprising first analog multiplexer 366 having input/output terminal Y coupled to transistor 352 and input/output terminal X coupled to transistors 358. As will be explained, multiplexer 366 routes motor drive signal applied at terminal O to either the X output or the Y output depending on the state of control terminal C. In this way either clockwise or counter-clockwise operation may be electronically selected. The motor drive logic circuit further includes second analog multiplexer 368 for controlling the motor direction and analog multiplexer 370 for selecting between different motor on/off signals depending on whether the aspirator mode or the cystotome mode has been selected. Analog multiplexers 368 and 370 both have control terminals C which are tied to the mode select bus 348. In the aspirator mode a low logic signal on bus 348 causes multiplexer 368 to couple terminal X with terminal O. Terminal O is in turn coupled to terminal C of multiplexer 366. Hence, in the aspirator mode signals applied to terminal X of multiplexer 368 control the motor direction. Conversely, when the unit is placed in the cystotome mode and a high logic signal is placed on bus 348, motor direction is controlled by signals applied to terminal Y of multiplexer 368. In a similar fashion multiplexer 370 is controlled by logic signals on bus 348. In the aspirator mode signals applied to terminal X of multiplexer 370 are routed through terminal O thereof to supply the motor on/off signal. In the cystotome mode signals applied to terminal Y of multiplexer 370 supply the motor on/off signal.

Having thus described the motor drive circuitry and motor logic circuitry, a description of the logic circuitry for implementing the aspirator mode will now be discussed. Inasmuch as it is highly desirable to be able to control the speed of the motor, thereby controlling the aspiration rate, a motor speed control circuit is included. Motor speed is controlled by pulse width modulation in which diodes 372 and 374 rectify the effective voltage on motor 44, regardless of which direction it is turning. More specifically, diode 372 is coupled to terminal E of jack 60 and polled to conduct current away from terminal E, whereas diode 374 is coupled to terminal F of jack 60 and polled to conduct current away from terminal F. The cathodes of diodes 372 and 374 are coupled together and thence coupled to filter circuit 376 comprising resistor 377 and capacitor 378. Filter 376 smoothes and filters the AC components of the rectified signals derives from the diodes to provide a signal to the input of analog multiplexer 380 which is proportional to the DC voltage across motor 44. The filtered signal is thus indicative of the driving speed of the motor, and current flow through the motor, and is used as a feedback signal for controlling the speed of the motor, as follows.

When the unit is switched in the aspirator mode and bus 348 is at a low logic level, multiplexer 380 couples the feedback signal from filter 376 applied to terminal X, via terminal O to the negative terminal 382 of comparator 384. To the positive terminal 386 of comparator 384 is coupled a reference signal or reference voltage. The reference voltage is supplied as at node 388 through voltage divider resistor 390. Node 388 is coupled to a precision voltage reference source 392, which may be implemented using an LM336Z-2.5 integrated circuit. Voltage divider resistor 390 is coupled at its other lead as at node 394 to terminal C of jack 60. Hence it will be seen that voltage divider resistor 390 and the motor speed control potentiometer 312 (connected to terminal C of jack 60 and to ground through terminal D thereof) form a resistive divider network and the voltage at node 394 may be varied directly by adjusting potentiometer 312.

Comparator 384 compares the adjustable reference signal at terminal 386 with the feedback signal at 382 to produce an error signal at its output terminal 396. This error signal is applied to terminal A of AND gate 398. A motor on signal, yet to be discussed, is applied at terminal B of AND gate 398 and the output thereof is coupled to terminal X of analog multiplexer 370, thereby providing a motor on signal to multiplexer 370 when the voltage across motor 306 falls below the reference voltage set by potentiometer 312, provided the motor on signal, yet to be discussed, is present at terminal B of AND gate 398.

With reference to jack 60, it will be seen that front switch 40-40' and back switch 42-42' are coupled respectively to terminals A and B of jack 60. Common switch lead 324 is coupled to terminal D thereof. Hence depressing either switch has the effect of pulling the corresponding jack terminal to ground. Terminals A and B of jack 60 are coupled to turn to comparators 399 and 400 which are wired as shown to act as signal conditioners for the respective front and back switches. The output of signal conditioning comparator 399 is applied to input terminal A of OR gate 402, while the output of signal conditioning comparator 400 is applied to the input terminal A of OR gate 404. In addition, the output of comparator 400 is also applied to input terminal B of AND gate 406, the output of which is in turn connected to input terminal B of OR gate 402. Furthermore, the output of comparator 399 is coupled to input terminal B of OR gate 408.

A backflush pulse generator or timer 410 is implemented using a timer circuit such as a 4538 integrated circuit. Capacitor 412, resistor 413 and variable resistor or potentiometer 414 provide the time base for the timer circuit. Potentiometer 414 may be manually varied by the operator to effect different degrees or rates of backflush. Backflush generator 410 includes a first input terminal A coupled to terminal A of OR gate 408 and a second terminal B coupled to terminal A of OR gate 402. The output of backflush generator 410 is provided at terminal Q and is coupled to terminal A of OR gate 408. The output of OR gate 408 is coupled in turn to input terminal B of OR gate 404. The output of OR gate 404 is coupled to input terminal B of AND gate 398.

Having thus described the electronic circuit for controlling the aspirator mode, a description of the electronic circuit for implementing the cystotome mode now follows. Through advantageous sharing of components, much of the circuits for implementing the cystotome mode has already been described in connection with the aspirator mode and will not be repeated. Accordingly, the electronic control circuit for implementing the cystotome mode further comprises a trio of timer circuits 416, 418 and 420. These timer circuits may be implemented using 4538 integrated circuits with appropriate timing capacitors 422, timing resistors 424, and a timing adjustment potentiometer 426 for adjusting the cycle delay characteristics of the circuit. Timer circuit 416 includes input terminal A coupled to the output of OR gate 402 and input B which is tied to complementary output terminal $\overline{Q}$ which is in turn coupled to input terminal X of analog multiplexer 428. The output Q of timer 416 is coupled to terminal Y of multiplexer 428 and is also coupled to input terminal B of timer 418. Input terminal A of timer 418 is tied to the Q output terminal thereof which is in turn coupled to terminal B of OR gate 430. Terminal A of OR gate 430 is coupled to the output terminal Q of timer 416. Terminal A of timer 420 is likewise tied to output terminal Q thereof while input terminal B is coupled to the output terminal Q of timer 418. The complementary output terminal $\overline{Q}$ of timer 420 is coupled back to terminal A of AND gate 406. The output of multiplexer 428 is connected to the Y input terminal of multiplexer 368. In addition, input terminal Y of multiplexer 380 is connected to resistive divider network 432 coupled between node 388 and ground, thereby providing an accurate reference signal.

Figure 12:
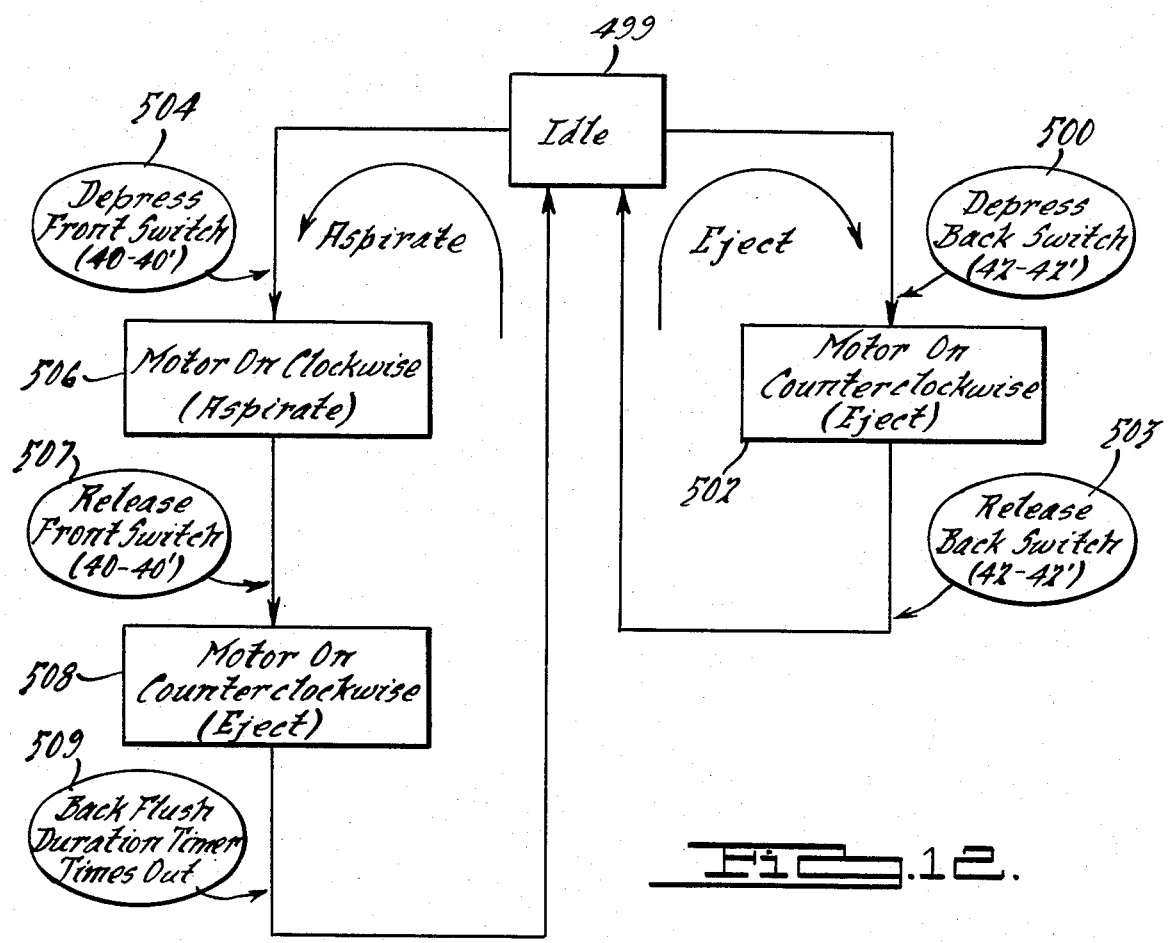
FIG. 12 is a state diagram for the operation of the present invention as an aspirator-irrigation mechanism.
Figure 13:
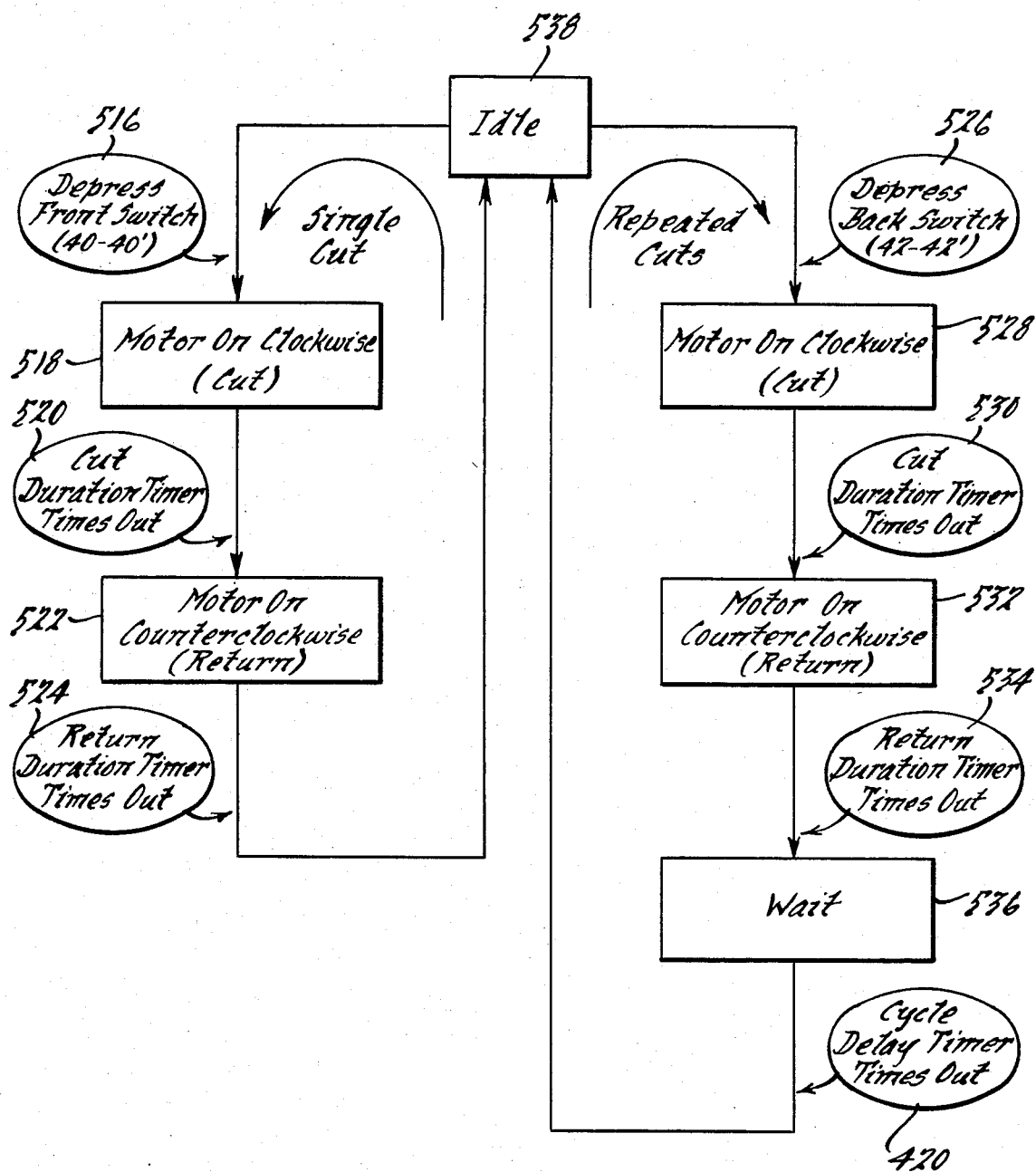
FIG. 13 is a state diagram for the operation of the present invention as a cystotome mechanism.

FIGS. 12 and 13 are state diagrams illustrating the operation of the invention in the aspirator mode and cystotome mode, respectively. With reference to FIG. 12, operation begins in the idle state 499, motor 44 is off and the instrument neither aspirates nor ejects. If the front switch 40–40' is depressed as indicated by event 504, motor 44 is turned on for rotation in a clockwise or aspirating direction as indicated by state block 506. Motor 44 will continue to rotate in a clockwise direection until front switch 40–40' is released, which is indicated by event 507. Once the front switch is released, the motor begins to rotate in a counterclockwise or ejecting direction, indicated by state block 508. When counterclockwise rotation begins, the backflush timer circuit 410 begins to count or measure the desired backflush duration in accordance with the manual setting of potentiometer 414. When the backflush duration timer times out, as indicated by event 509, motor 44 returns to the idle state 499.

If instead the back switch 42–42' is depressed, as indicated by event 500, motor 44 commences rotation in a counterclockwise or ejecting direction as indicated by state block 502. Motor 44 will continue to rotate in the conterclockwise direction until back switch 42–42' is released, indicated by event 503. When this event occurs the motor returns to the idle state 499.

Referring now to FIG. 13, the cystotome mode may also be illustrated commencing in the idle state 538. If front switch 40–40' is depressed, event 516, motor 44 is turned on for rotation in the clockwise or cutting direction indicated in state block 518. When motor 44 commences clockwise rotation the cut duration timer 416 commences timing the cut duration, and when timer 416 times out as indicated by event 520 the motor commences rotation in a counterclockwise or return direction, state 522. When the motor commences its counterclockwise rotation the return duration timer 418 commences timing the return duration. When return duration timer 418 times out (event 524) the motor returns to the idle state 538.

If, on the other hand, the back switch 42–42' is depressed (event 526) a series of repeated cuts will be performed as follows. Depressing back switch 42–42' causes motor 44 to turn on and rotate in a clockwise or cutting direction indicated by block 528. When motor 44 commences clockwise rotation, the cut duration timer 416 begins timing, and when it times out (event 530), motor 44 commences counterclockwise rotation or return rotation as indicated by state block 532. As counterclockwise rotation is commenced, the return duration timer 418 commences timing and when timer 418 times out, (event 534) motor 44 enters a pause state or waiting state 536. Upon entering the waiting state 536, the cycle delay timer 420 commences timing or counting in accordance with the manual setting of potentiometer 426. When the cycle delay timer 420 times out (event 537) the motor returns to the idle state 538, whereupon the cycle repeats so long as switch 42–42' remains depressed.

In operation the user has the option of selecting either the aspirator mode or the cystotome mode by setting switch 330 appropriately. Assuming the aspirator mode has been selected, switch 330 applies power to the unit and turns on light emitting diode 344. The voltage at bus 348 is thus at a low logic level which toggles multiplexers 368, 370 and 380 into a first state whereby their X and O terminals are coupled together to provide an analog signal path.

Assume for the moment that back switch 42–42' is depressed. In the aspirator mode this corresponds to a counter-clockwise motor command which causes fluid to be ejected from the syringe-type tube 92. This action is illustrated in the state diagram block 502 of FIG. 12. By depressing back switch 42–42' terminal B of jack 60 is pulled to ground, thereby placing a high logic signal on the output of comparator 400. This high logic signal passes through OR gate 404 and provides a motor on command signal to AND gate 398. Because the motor was not running when switch 42–42' was depressed, the output of comparator 384 is high, hence the output of AND gate 398 is also high and the motor on signal is thus applied to terminal X of multiplxer 370. Through multiplexer 370 the motor on signal is applied to multiplexer 366, which functions to route the motor on signal to either transistor 352 or transistor 358, depending on whether clockwise rotation or counter-clockwise rotation is required. Because the back switch 42–42' has been depressed the X terminal of multiplexer 368 is at a low logic level. This low logic level is routed via terminal O of multiplexer 368 to the control terminal C of the direction decoder multiplexer 366. A low logic signal at terminal C causes decoder multiplexer 366 to couple the motor on signal through terminal X to transistor 358. The motor is thus driven in a counter-clockwise direction causing the tube 92 to eject fluid therefrom.

The speed of the motor 44 is controlled by pulse width modulation. Diodes 372 and 374 rectify the effective voltage on the motor (and thus indirectly measure the current flow through the motor). Because both diodes are polled to conduct current away from respective motor terminals E and F, the diodes provide a signal indicative of the motor speed regardless of which direction the motor is turning. Filter network 376 filters the AC components from this motor speed signal to provide a signal to the input of multiplexer 380 which is proportional to the DC voltage on the motor, and hence indicative of the current flow through the motor and the motor speed. Multiplexer 380 conducts the signal via terminal O to comparator 384. Comparator 384 compares the motor speed signal to the reference signal derived from voltage reference source 392. Motor speed control potentiometer 312, together with resistor 390, serves as a voltage divider to provide a reference signal at the input 386 of comparator 384 which is indicative of the manually selected speed or the desired speed of the motor. The output of comparator 384 is, as mentioned above, applied to terminal A of AND gate 398. Hence if the voltage across the motor falls below the reference voltage set by potentiometer 312 a high logic signal will be applied to terminal A of AND gate 398. If a motor on (high logic signal) is also indicated at terminal B of AND gate 398, the output of AND gate 398 is high and the motor is thereby energized.

Now assuming that the front switch 40-40' is depressed, corresponding to an aspiration command 504 as shown in FIG. 12, the motor will turn in a clockwise or aspirating direction as shown by box 506. Depressing front switch 40-40' causes the output of comparator 399 to go high. This high logic signal is applied to terminal X of multiplexer 368 which conveys the signal via terminal O to the control terminal C of multiplexer 366. A high logic signal on terminal C toggles direction decoder multiplexer 366 to its second state whereby motor on signals are conveyed from terminal O to terminal Y. Hence motor on signals will be applied to transistors 352 causing the motor to turn in a clockwise direction. When front switch 40-40' is depressed and the output of comparator 399 is high, motor on signals are derived from OR gate 408 and in turn applied to OR gate 404. Motor on signals from OR gate 404 are in turn applied to AND gate 398 which provides motor speed control through pulse width modulation as described above.

Upon deactivation of front switch 40-40', terminal B of backflush generator 410 returns to a low logic level. This causes the one shot timer circuit to be triggered and a pulse is generated through output Q and hence applied to OR gate 408 to provide a momentary motor on signal of a duration controlled by the setting of potentiometer 414 in the timer circuit. However, since front switch 40-40' is now deactivated and a low logic signal appears at terminal X of multiplexer 368, direction decoder multiplexer 366 is toggled back to the counter-clockwise state so that the momentary motor on signal generated by backflush generator 410 is routed out through terminal X of multiplexer 366 to momentarily energize transistor 358, thereby momentarily driving the motor in a counter-clockwise direction. This has the effect of ejecting a small quantity of fluid and/or particulant matter previously drawn into the syringe-type tube 92 during aspiration.

By switching switch 330 to the cystotome mode, light emitting diode 346 is lit and power supplied to the unit. This time, however, a high logic signal appears on bus 348 which toggles multiplexers 368, 370 and 380 to the other state whereby terminals O and Y are connected to provide an analog signal path. Hence, for example, multiplexer 380 is no longer connected to the rectifier diodes 372 and 374, but is instead connected to voltage divider network 432 which provides a preset reference voltage causing the motor to run at full speed.

In the cystotome mode the functions of front and back switches 40-40' and 42-42' as well as potentiometer 312 are redefined. Front switch 320 whose output is conditioned by comparator 399 causes cut delay time or cut duration, set by one shot timer 416, to commence. After timer 416 times out (event 520 of FIG. 13) it triggers the return delay time or return duration set by one shot timer 418. If either timer 416 or 418 are turned on, the output of OR gate 430 is at a high logic level and the motor is turned on at full speed. The motor proceeds in one direction for the duration of the timer 416 output pulse and then proceeds in the opposite direction for the duration of the timer 418 output pulse. This operation is illustrated by events 516, 520 and 524 and state blocks 518 and 522 in FIG. 13.

The motor rotation direction or cutting direction is controlled by the output of timer 416 in accordance with the setting of potentiometer 312. Comparator 384 compares the voltage across the voltage divider comprised of resistor 390 and potentiometer 312 to the fixed reference voltage applied at terminal 382 (derived from voltage divider network 432). If the potentiometer 312 is rotated counter-clockwise so that it points left of center the output of comparator 384 is high, and if the potentiometer is rotated clockwise so as to point right of center the output of comparator 384 is low. When the output of comparator 384 is high multiplexer 428 routes the output of timer 416 to the direction selector input, i.e., terminal Y of multiplexer 368. If the output of comparator 384 is low, multiplexer 428 routes the complement of the output of timer 416 to the direction selector input terminal Y of multiplexer 368.

By depressing back switch 42-42' a series of repeated cuts can be performed, as illustrated by events and state blocks 526 through 420 of FIG. 13. By comparison with single cut operation (events and states 516-524), the repeated cut operation includes a Wait state 536 or delay between repeated cuts. This Wait state is timed by timer 420. When back switch 322 is depressed, AND gate 406 routes the output of one shot timer 420 back to the input of one shot timer 416 to cause the cut and return cycle to start again. The cycle will repeat so long as switch 42-42' is depressed. After timer 418 times out it triggers timer 420 for a duration set by the user by adjusting potentiometer 426. Potentiometer 426 causes a variable pulse between cycle repeats.

To assure precision in either the aspirator mode or the cystotome mode, comparator 480 compares the internal precision voltage reference as at node 388 to the battery voltage applied at node 482 and turns on low battery indicator LED 484 appropriately. To assure that the logic circuits are not interfered with by fluctuations caused by the motor current requirements, logic supply voltages are filtered by resistors 486 and capacitor 488.

The foregoing discussion discloses and describes merely exemplary embodiments of the present invention. One skilled in the art will readily recognize from such discussion that various changes, modifications and variations may be made therein without departing from the spirit and scope of the invention as defined in the following claims.

We claim:

1. An ophthalmic irrigator-aspirator comprising; a handpiece, a bidirectional motor means disposed within said handpiece, a drive shaft coupled to said motor means, syringe means having a tube and an opening in one end thereof, a piston internally disposed within said tube, said piston having means cooperating with said drive shaft such that said piston is translatable within said tube in a direction causing aspiration through said tube opening as said motor means is rotated in one direction, and causing irrigation through said tube opening when said motor means is rotated in an opposite direction, and manually actuable means on said handpiece for causing rotation of said motor means in either rotational direction.

2. The ophthalmic aspirator of claim 1 wherein said syringe means is detachably carried on said handpiece.

3. The ophthalmic aspirator of claim 1 wherein said syringe means includes coaxial cannula tube means having an inner tube communicating with said syringe means, and outer coaxial tube means communicating with a source of fluid.

4. The ophthalmic aspirator of claim 1 further comprising means for controlling the speed of said motor means.

5. The ophthalmic aspirator of claim 4 wherein said means for controlling the speed of said motor means includes manual control means disposed on said handpiece.

6. The ophthalmic aspirator of claim 1 further comprising backflush means responsive to said manually actuable means for reversing the aspiration.

7. The ophthalmic aspirator of claim 6 wherein said backflush means includes means for automatically reversing the aspiration in response to the release of said manually actuable means.

8. An ophthalmic aspirator comprising syringe means having a tube with an internally disposed slidable piston, and motor means installed within a handpiece, a drive shaft coupled to said motor means, said drive shaft coupled to said slidable piston for driving said slidable piston within said tube in either an aspirating direction or an ejecting direction, first and second manually operable switching means, and circuit means couplable to a source of electrical current and responsive to said first switching means for causing current flow through said motor means in a first direction thereby energizing said motor means to drive said piston in said aspirating direction and further responsive to said second switching means for causing current flow through said motor means in a second direction thereby energizing said motor means to drive said piston in said ejecting direction.

9. The aspirator of claim 8, wherein said circuit means includes means for modulating said current flow through said motor means.

10. The aspirator of claim 9, wherein said means for modulating produces pulsed signals of variable pulse width and said circuit means includes manually adjustable speed control means for varying said pulse widths, thereby controlling the driving speed of said motor means.

11. The aspirator of claim 8, further comprising means for generating a reference signal, feedback means coupled to said motor means for providing a feedback signal indicative of the driving speed of said motor means and comparator means receptive of said reference signal and said feedback signal for modulating said current flow through said motor means.

12. The aspirator of claim 11, wherein said feedback means comprises rectifying means coupled to said motor means and filter means coupled to said rectifying means for providing an analog signal indicative of said current flow through said motor means.

13. The aspirator of claim 8, further comprising backflush means responsive to said first switching means for momentarily driving said syringe means in said ejecting direction.

14. The aspirator of claim 13, wherein said backflush means comprises manually operable control means and one shot means responsive to said control means and to said first switching means for producing a pulse having a duration variable in accordance with said control means.

15. The aspirator of claim 8, further comprising cystotome means coupled to said motor means for movement in cutting and return directions, mode selection means coupled to said circuit means and first timer means enabled by said mode selection means for activating said motor means into alternate movement in said cutting and return directions.

16. The aspirator of claim 15, further comprising second timer means coupled to said first timer means for repetitive triggering of said first timer means.

* * * * *

UNITED STATES PATENT AND TRADEMARK OFFICE
CERTIFICATE OF CORRECTION

PATENT NO. : 4,508,532

DATED : April 2, 1985

INVENTOR(S) : Robert C. Drews; Danny D. Meyer; Tadmor Shalon; Eliezer Pasternak

It is certified that error appears in the above-identified patent and that said Letters Patent is hereby corrected as shown below:

Column 2, line 64, "digram" should be --diagram--

Column 7, line 45, "postion" should be --position--

Column 10, line 49, "to" (first occurrence) should be --in--

Signed and Sealed this

Tenth Day of December 1985

[SEAL]

Attest:

DONALD J. QUIGG

Attesting Officer

Commissioner of Patents and Trademarks